US005906573A

United States Patent [19]
Aretz

[11] Patent Number: 5,906,573
[45] Date of Patent: May 25, 1999

[54] RADIOACTIVE SURGICAL FASTENING DEVICES AND METHODS OF MAKING SAME

[75] Inventor: H. Thomas Aretz, Brookline, Mass.

[73] Assignee: RadioMed Corporation, Burlington, Mass.

[21] Appl. No.: 08/897,080

[22] Filed: Jul. 18, 1997

[51] Int. Cl.[6] ........................................................ A61N 5/00
[52] U.S. Cl. ................................ 600/3; 606/60; 606/76; 606/151
[58] Field of Search .............................. 600/1–8; 606/60, 606/65, 67, 69, 70, 72–75, 76, 77, 151, 153–54, 157, 228, 230, 231

[56] References Cited

U.S. PATENT DOCUMENTS

| | | | |
|---|---|---|---|
| 2,153,889 | 4/1939 | Hames | 128/1.1 |
| 4,509,506 | 4/1985 | Windorski et al. | 128/1.2 |
| 5,059,166 | 10/1991 | Fischell et al. | 600/3 |
| 5,176,617 | 1/1993 | Fischell et al. | 600/3 |
| 5,199,939 | 4/1993 | Dake et al. | 600/3 |
| 5,302,168 | 4/1994 | Hess | 600/3 |
| 5,354,257 | 10/1994 | Roubin et al. | 600/7 |
| 5,411,466 | 5/1995 | Hess | 600/3 |
| 5,468,562 | 11/1995 | Farivar et al. | 428/457 |
| 5,474,797 | 12/1995 | Sioshansi et al. | 427/2.24 |
| 5,484,384 | 1/1996 | Fearnot | 600/3 |
| 5,492,763 | 2/1996 | Barry et al. | 428/457 |
| 5,498,227 | 3/1996 | Mawad | 600/3 |
| 5,503,613 | 4/1996 | Weinberger | 600/3 |
| 5,520,664 | 5/1996 | Bricault, Jr. et al. | 604/265 |
| 5,540,659 | 7/1996 | Teirstein | 604/104 |
| 5,556,389 | 9/1996 | Liprie | 604/264 |
| 5,607,442 | 3/1997 | Fischell et al. | 606/191 |
| 5,709,644 | 1/1998 | Bush | 600/3 |

OTHER PUBLICATIONS

Amols, "Advances In Cardiovascular Radiation Therapy, Debate: The Preferred Isotope Source—Beta Vesus Gamma?", Washington, D.C., p. 64, Feb. 20–21, 1997.

Amols et al., "Dosimetric Considerations For Catheter–Based Beta And Gamma Emitters In The Therapy Of Neointimal Hyperplasia In Human Coronary Arteries", *Int. J. Radiation Oncology Biol. Phys.*, vol. 36, No. 4, pp. 913–921, 1996.

Brenner et al., "The Radiology Of Intravascular Irradiation", *Int. J. Radiation Oncology Biol. Phys.*, vol. 36, No. 4, pp. 805–810, 1996.

Califf et al., "Restenosis After Coronary Angioplasty: An Oveview", *JACC*, vol. 17, No. 6, pp. 2B–13B, May, 1991.

Carter et al., "Experimental Results With Endovascular Irradation Via A Radioactive Stent", *Int. J. Radiation Oncology Biol.*, vol. 36, No. 4, pp. 797–803, 1996.

Coffey et al., "Advances in Cardiovascular Radiation Therapy, The Physics of Beta Emitting Radioactive Stents", Washington, D.C., p. 124, Feb. 20–21, 1997.

Condado et al., "Advances in Carciovascular Radiation Therapy, Two Year Follow-Up After Intracoronary Gamma Radiation", Washington, D.C., p. 163, Feb. 20–21, 1997.

Crilly et al., "Advances in Carciovascular Radiation Therapy, Abstract #11, The Effect of Calcification in Atherosclerotic Lesions on the Dose Distribution of Axially Delivered β and γ Radiation", Washington, D.C., p. 12, Feb. 20–21, 1997.

Darzi et al., "Evaluation of Various Methods of Treating Keloids and Hypertrophic Scars: A 10–year Follow–up Study", *British Journal of Plastic Surgery*, vol. 45, pp. 374–379, 1992.

Doornbos et al., "The Role of Kilovoltage Irradiation in the Treatment of Keloids", *Int. J. Radiation Oncology Biol. Phys.*, vol. 18, pp. 833–839, 1990.

Eigler et al., "Advances In Cardiovascular Radiation, Experiences With A Radioactive Stent," Washington, D.C., p. 137, Feb. 20–21, 1997.

Eigler et al., "Advances in Carciovascular Radiation Therapy, A Radioactive Nitinol Stent", Washington, D.C., pp. 138–139, Feb. 20–21, 1997.

Fischell, Advances in Carciovascular Radiation Therapy, Insights From IRIS (Isostent for Restenosis Intervention Study), Washington, D.C., p. 130, Feb. 20–21, 1997.

Fischell, "Advances in Carciovascular Radiation Therapy, Insights From IRIS (Isostent for Restenosis Inervention Study)", Washington, D.C., pp. 131–136, Feb. 20–21, 1997.

Fitzgerald et al., "Dosimetry Of Auricular Keloid Irradiation", *Radiology*, vol. 144, pp. 651–652, Aug., 1982.

Gravanis et al., "Intracoronary Low–Dose Ionizing Irradiation (β or γ) For Prevention Of Restenosis: Could It Succeed Where Pharmacotherapy Failed?", *Cardiovasc Pathol*, vol. 6, No. 1, pp. 11–21, Jan./Feb., 1997.

Hehrlein, "Advances In Cardiovascular Radiation Therapy, The European Experience With Radioactive Stents", Washington, D.C., p. 125, Feb. 20–21, 1997.

Hehrlein et al., "Advances In Cardiovascular Radiation Therapy, Low Dose Radioactive Endovascular Stents Prevent Smooth Muscle Cell Proliferation and Neointimal Hyperplasia In Rabbits", Washington, D.C., pp. 126–127, Feb. 20–21, 1997.

Hehrlein et al., "Advances In Cardiovascular Radiation Therapy, Pure β–Particle–Emitting Stents Inhibit Neointima Formation In Rabbits", Washington, D.C., p. 128, Feb. 20–21, 1997.

King, "Advances In Cardiovascular Radiation Therapy, The BERT (Beta Energy Restenosis Trial) Feasibility Study", Washington, D.C., pp. 164–166, Feb. 20–21, 1997.

Klumpar et al., "Keloids Treated With Excision Followed By Radiation Therapy", *J. Am. Acad. Dermatol.* vol. 31, pp. 225–231, 1994.

Kovalic et al., "Radiation Therapy Following Keloidectomy: A 20–Year Experience", *Int. J. Radiation Oncology Biol. Phys.*, vol. 17, pp. 77–80, 1989.

(List continued on next page.)

*Primary Examiner*—John P. Lacyk
*Attorney, Agent, or Firm*—Lappin & Kusmer LLP

[57] ABSTRACT

A surgical fastening device, such as a suture, staple, clip, pin or the like, is rendered therapeutically radioactive in order to inhibit cellular proliferation at a wound or surgical repair site, by implantation of a radioisotope into the material of the device. The device can be made of any material, including metals, nonmetals, plastics and ceramics.

32 Claims, 1 Drawing Sheet

OTHER PUBLICATIONS

Li et al., "Advances In Cardiovascular Radiation Therapy, Calculation of the Detailed Dose Distribution Surrounding A Beta–Emitting Nitinol Stent: Validation of Intravascular Mini–Dosimetry Using Radiochromic Film", Washington, D.C., p. 9, Feb. 20–21, 1997.

Liermann, "Advances In Cardiovascular Radiation Therapy, Six Year Follow–up After Brachytherapy in Femoral Arteries: The Frankfurt Experience", Washington, D.C., p. 148, Feb. 20–21, 1997.

Liermann, "Advances In Cardiovascular Radiation Therapy, Brachytherapy to Treat Restenosis in Peripheral Arteries— Long Term Follow–up", Washington, D.C., pp. 149–153, Feb. 20–21, 1997.

Ma et al., "Measurement Of Radiation–Induced DNA Double–Strand Breaks in Human Diploid Fibroblasts From Keloid and Normal Skin by Single–Cell Gel Electrophoresis", *Plast. Reconstr. Surg.*, vol. 98, No. 5, pp. 821–826, Oct. 1996.

Mazur et al., "High Dose Rate Intracoronary Radiation For Inhibition Of Neointimal Formation In The Stented And Balloon–Injured Porcine Models Of Restenosis: Angiographic, Morphometric, And Histopathologic Analyses", *Int. J. Radiation Oncology Biol. Phys.*, vol. 36, No. 4, pp. 777–788, 1996.

Murray et al., "Keloids: A Review", *J. Am. Acad Dermatol.*, vol. 4, pp. 461–470, Apr., 1981.

Popowski et al., "A Novel System For Intracoronary β–Irradiation: Description And Dosimetric Results", *Int. J. Radiation Oncology Biol. Phys.*, vol. 36, No. 4, pp. 923–931, 1996.

Quast et al., "Advances In Cardiovascular Radiation Therapy, Abstract #7, Fast 3D Dosimetric Treatment Planning The Solution For Precise Cardiovascular β–Radiotherapy", Washington, D.C., p. 8, Feb. 20–21, 1997.

Raizner, "Advances In Cardiovascular Radiation Therapy, Endovascular Radiation Using HDR With Beta and Gamma Sources in the Porcine Model", Washington, D.C., pp. 99–101, Feb. 20–21, 1997.

Rubin et al., "Editor's Note", *Int. J. Radiation Oncology Biol. Phys.*, vol. 36, No. 4, pp. 763–766, 1996.

Sioshansi, "Tailoring Surface Properties By Ion Implantation", Materials Engineering, Ion Implantation, *Penton Publishing*, Feb., 1997.

Sioshansi, "Surface Engineering By Ion Implantation", Precision Metal, *Penton Publishing*, Dec., 1988.

Smith et al., "Advances In Cardiovascular Radiation Therapy, Abstract #19, Efficiency of a Re–186 Filled PTCA Balloon System To Prevent Restenosis Of Peripheral Vessels In Swine and A–V Grafts in Sheep", Washington, D.C., p. 20, Feb. 20–21, 1997.

Styles et al., "Advances In Cardiovascular Radiation, Therapy, Abstract #10, Effects of External Irradiation of the Heart on the Coronary Artery Response to Balloon Angioplasty Injury in Pigs", Washington, D.C., p. 11, Feb. 20–21, 1997.

Teirstein, "β–Radiation To Reduce Restenosis, Too Little, Too Soon?", *Circulation*, vol. 95, No. 5, pp. 1095–1097, Mar. 4, 1997.

Terstein et al., "Advances In Cardiovascular Radiation Therapy, Intracoronary Catheter–Based Gamma Radiation The SCRIPPS Trial", Washington, D.C., pp. 169–170, Feb. 20–21, 1997.

Urban et al., "Advances In Cardiovascular Radiation Therapy, The Swiss 90 Yttrium Study", Washington, D.C., p. 161, Feb. 20–21, 1997.

Verin et al., "Advances In Cardiovascular Radiation Therapy, Intra–arterial Beta Irradiation Prevents Neointimal Hyperplasia in a Hypercholesterolemic Rabbit Restenosis Model," Washington, D.C., p. 162, Feb. 20–21, 1997.

Verin et al., "Feasibility of Intracoronary β–Irradiation To Reduce Restenosis After Balloon Angioplasty, A Clinical Pilot Study", *Circulation*, vol. 95, No. 5, pp. 1138–1144, Mar. 4, 1997.

Virmani et al., "Advances In Cardiovascular Radiation Therapy, Histopathological Responses After Radioactive Stent Placement In Animals," Washington, D.C., p. 129, Feb. 20–21, 1997.

Waksman et al., "Endovascular Low–Dose Irradiation Inhibits Neointima Formation After Coronary Artery Balloon Injury in Swine", *Circulation*, vol. 91, No. 5, pp. 1533–1539, Mar. 1, 1995.

Waksman, "Advances In Cardiovascular Radiation Therapy, Brachytherapy For AV–Dialysis Shunts and Superficial Femoral Arteries: U.S. Pilot Studies", Washington, D.C., pp. 154–155, Feb. 20–21, 1997.

Waksman, "Advances In Cardiovascular Radiation Therapy, Catheter–Based Systems For Stented Arteries", Washington, D.C., pp. 140–141, Feb. 20–21, 1997.

Waksman, "Advances In Cardiovascular Radiation Therapy, Lessons Learned From Animal Studies", Washington, D.C., pp. 92–97, Feb. 20–21, 1997.

Weinberger et al., "Intracoronary Irradiation: Dose Response For The Prevention Of Restenosis In Swine", *Int. J. Radiation Oncology Biol. Phys.*, vol. 36, No. 4, pp. 767–775, 1996.

Weintraub, "Evaluating The Cost Of Therapy For Restenosis: Considerations For Brachytherapy", *Int. J. Radiation Oncology Biol. Phys.*, vol. 36, No. 4, pp. 949–958, 1996.

Wilcox et al., "The Role of The Adventitia In The Arterial Response To Angioplasty: The Effect Of Intravascular Radiation", *Int. J. Radiation Oncology Biol. Phys.*, vol. 36, No. 4, pp. 789–796, 1996.

Xu et al., "The Dose Distribution Produced By a $^{32}$P Source For Endovascular Irradiation", *Int. J. Radiation Oncology Biol. Phys.*, vol. 36, No. 4, pp. 933–939, 1996.

ns surrounding implantable medical
RADIOACTIVE SURGICAL FASTENING DEVICES AND METHODS OF MAKING SAME

CROSS-REFERENCE TO RELATED APPLICATIONS

This application is related to provisional U.S. application Ser. No. 60/049961, filed on Jun. 17, 1997.

TECHNICAL FIELD

The invention is directed to devices and methods for incorporating radioisotopes into medical devices, and particularly surgical fastening devices, for the inhibition of cellular proliferation.

BACKGROUND OF THE INVENTION

Through long evolution, the human body has developed very sophisticated, complex and effective defense mechanisms against injury and disease. Nevertheless, sometimes these mechanisms can result in undesirable consequences, as, for example, when histamines are liberated in response to an allergen, or when transplanted organs are rejected by the immune system.

Perhaps the most common defense mechanism is the replacement of tissue when cells are destroyed by injury or disease. This mechanism can also engender phenomena which are, in effect, counter-productive. Whereas the normal acute inflammatory reaction in response to cellular injury is essential to survival in traumatic situations, that same mechanism can lead to an excessive response which exceeds its intent. Examples of these excessive responses include keloids of the skin, adhesions of organs to surrounding tissues following injury or surgery, stricture formation in hollow conduits such as ureters, fallopian tubes, and bile ducts, and contractures surrounding implantable medical devices.

The trauma induced by the well-known procedures of angioplasty or stenting for treatment of flow restrictions in the cardiovascular system can result in failure of the procedure by restenosis, or blockage, of the vessel soon afterwards. Vascular grafts used to relieve blood flow restrictions, to treat aneurysms, or to provide access for conduits needed for dialysis also can become blocked by intimal hyperplasia, or cellular proliferation, after insertion of the graft into the body. Even surgery on the skin can result in the undesirable phenomenon of scar tissue formation which, while seldom life-threatening, can result in disfigurement. All of these phenomena are manifested by a proliferation of cells, typically smooth muscle cells and/or fibroblasts, to an extent which exceeds the requirement for successful healing of the injury.

It has been discovered that ionizing radiation can address and temper the crucial final mechanism of restenosis. Radiation inhibits cell proliferation by preventing replication and migration of cells and by inducing programmed cell death (apoptosis).

Cells are variably susceptible to radiation, dependent on the types of cells and their proliferative status. Rapidly proliferating cells are generally more radiation-sensitive, whereas quiescent cells are more radiation-tolerant. High doses of radiation can kill all functions of even quiescent cells, whereas lower levels can merely lead to division delays. However, the desirable effect of reproductive death still obtains. In this case, the cell remains structurally intact but has lost its ability to proliferate, or divide indefinitely. It appears that low level radiation produces this desirable effect without causing tissue destruction or wasting (atrophy). In addition, the choice of isotopes allows for the local application of predictable doses of radiation with known depths of penetration and times of application, which are the factors that govern the biological effects of radiation.

Radiation treatment (usually known as "brachytherapy" when used for cancer treatment) is well-established for the treatment of cancer, a malignant form of cellular proliferation. Radiation treatment is also generally considered by the medical community to be effective in controlling the healing response. In particular, there appears to be general agreement among the interventional cardiology community that focused interluminal radiation can significantly reduce the restenosis problem.

Abbass et al., in their pioneering work, showed the effect of external radiation in retarding cell proliferation following percutaneous transluminal coronary angioplasty (PTCA). To avoid the complexities involved in the use of external radiation sources, several groups have investigated the brachytherapy approach by using an internal source of radiation. In particular, Fischell et al. have shown that the use of low-intensity (on the order of 10 microcuries, which is less radiation than the amount of radiation involved with angiography), low-energy beta emitters (average energy of 0.69 MeV) and short-lived (14.3 day half life) $^{32}$p in animal studies have significantly reduced neointimal regrowth. Similarly, the effectiveness of brachytherapy in connection with the interoperative use of a radioactive coronary guidewire to retard intimal hyperplasia is known. For example, U.S. Pat. No. 5,498,227 to Mawad discloses the use of a radioactive wire intended for use in the delivery of a dose of radiation to a lesion or other body tissue. The wire includes an inner radioactive core surrounded by an outer buffer layer of platinum or other high atomic number metal to attenuate the radiation. The wire is made radioactive by incubation in a nuclear accelerator for a specified period of time prior to its implantation into the body.

Attention is currently being directed to the practical aspects of the use of brachytherapy. These aspects are, of course, particularly significant when radioactivity is involved. A portion of the patient may be exposed to radiation either before or during an operative procedure. Alternatively, the radioactivity may be incorporated into an implanted device. In the first case, higher intensities of radiation are needed, which pose safety and handling problems. In the second case, the implanted devices are typically quite expensive. If radioactivity is added to the device, it is only effective during a relatively short period during which the radioactivity is provided at a useful (therapeutic) level. The device is not useful if the radioactivity has decayed to a level which is below the therapeutic minimum dosage level. Depending on the radioisotope used, the decay time may be in hours, days or weeks.

Currently, despite the rapidly increasing interest in the use of low-level radioactivity for the inhibition of cellular proliferation, there is no commercial source of radionuclide ion implantation for medical devices anywhere in the world. The rapidity with which this need is developing is evidenced from numerous publications, well-attended conferences and clinical studies now under way. Despite the obvious potential improvement in medical economics and patient outcomes represented by these applications, their approaching commercialization will impose a manufacturing requirement that is as yet unfulfilled in any practical manner.

Although there still remain proponents of the use of external radiation beams for this purpose, most prospective users and suppliers involved with intervascular radiotherapy would prefer to use only the minimum level of radioactivity necessary for effectiveness. This requires that the radioisotope be as localized as possible, preferably incorporated into a surgical fastening device (such as a suture, staple, clip, pin, plate, graft, or patch, etc.) which closely approximates the site to be treated.

It is known to use a surgical suture in combination with a radiation source in order to apply a therapeutic dose of radiation to a specific treatment site for cancer treatment. For example, U.S. Pat. No. 2,153,889 to Hames discloses a nonabsorbable tubular woven suture material which acts as a carrier vehicle for discrete radioactive seeds, which are spaced apart from one another along a length of the suture. The radioactive seeds are maintained in place at the treatment site with the suture until the desired radiation dose is delivered, after which the suture is withdrawn. U.S. Pat. No. 4,509,506 to Windorski et al. discloses an absorbable suture material which contains and acts as a carrier vehicle for radioactive seeds for cancer treatment.

A disadvantage of these prior art sutures is that, because they are merely carrier vehicles for radioactive seeds, the seeds must be specifically placed and distributed in a desired spacing along the sutures. This requires substantial labor in the manufacture of the suture. In addition, the radiation dose is nonuniformly distributed to the treatment region as a result of the spacing between radioactive seeds in the suture. Other problems include the relatively large diameter required for a suture which must contain the radioactive seeds within an inner lumen. The possibility exists that the radioactive seeds within the inner lumen will become dislodged, resulting in the migration and leaching of radioactivity into tissues remote from the treatment site.

The provision of other types of surgical fastening devices, including staples, clips, pins, plates and patches, in combination with a source of radiation would be an advancement in the art.

The incorporation of a source of radiation into a polymeric carrier is also known. U.S. Pat. No. 5,199,939 to Dake et al. discloses an elongated catheter or carrier which houses a radiation source, which can be placed onto or into the carrier or manufactured into the material of the carrier. Integration of a radioisotope into the material of a metallic stent is also known. See, for example, U.S. Pat. Nos. 5,059,166 and 5,176,617 to Fischell et al., which disclose the integration of a radioisotope into the stent material by alloying or coating processes. It is further known to employ ion implantation methods to integrate metal atoms into nonmetallic substrates. See, for example, U.S. Pat. No. 5,520,664 to Bricault, Jr. et al., which discloses the use of ion beam assisted deposition (IBAD) techniques to incorporate an antimicrobial metal, such as silver, into the surface of a polymeric catheter.

However, the use of ion implantation methods to incorporate a radioisotope into various metallic and nonmetallic surgical fastening devices has been heretofore unknown.

SUMMARY OF THE INVENTION

According to one aspect of the invention, there is provided a surgical fastening device capable of controlling cellular response to injury at a wound repair site in a patient. The device comprises a biocompatible surgical fastening device which can be implanted in the patient at or near the wound repair site, and a radiation source incorporated into at least a portion of the fastening device to render it radioactive.

The radioactive device is selectively positionable with respect to the wound repair site for delivery of a predetermined dose of radiation to the wound repair site.

The surgical fastening device is selected from the group consisting of sutures, staples, clips, pins, nails, screws, plates, barbs, anchors, and patches.

In one embodiment, the device is made of a metallic material. In another embodiment, the device is made of a substantially nonmetallic material, such as a polymeric material or a material which is substantially bioabsorable.

The surgical fastening device may be substantially permanently implantable in the patient. Alternatively, it may be adapted for temporary or removable implantation in the patient.

In a preferred embodiment, the radiation source comprises a radioisotope which can be incorporated into the surgical fastening device by ion implantation. An encapsulating layer of a coherent, biocompatible, and relatively dense material can optionally be deposited onto the surface of the surgical fastening device after ion implantation of the radioisotope into the fastening device. The encapsulating layer preferably comprises a biologically benign material selected from the group consisting of platinum, titanium, gold, palladium, stainless steel, nickel-titanium alloys, silica, and alumina.

According to another aspect of the invention, there is provided a method of controlling cellular response to injury at a wound repair site in a patient. The method comprises the steps of:

a. providing a surgical fastening device for controlling the cellular response to injury, wherein the device includes a biocompatible surgical fastening device which can be implanted in the patient at or near the wound repair site, and a radiation source incorporated into at least a portion of the surgical fastening device to render it radioactive; and b. implanting the surgical fastening device in the patient at or near the wound repair site. The radiation source is selected to deliver a predetermined dose of radiation to the wound repair site over a predetermined period of time.

In one embodiment, the method can include the further step of removing the surgical fastening device from the patient after the predetermined dose of radiation has been delivered to the wound repair site.

In a preferred embodiment, the surgical fastening device is a suture. In this case the method can include the further steps of:

c. providing a mesh or gauze suitable for application to the wound repair site; and d. securing the mesh or gauze to living tissue at the wound repair site with the suture, wherein a predetermined dose of radiation is delivered to the graft/tissue interface over a predetermined period of time.

According to still another aspect of the invention, there is provided a kit for controlling cellular response to injury at a wound repair site in a patient. The kit comprises:

a) a biocompatible surgical fastening device which is implantable in the patient at or near the wound repair site;

b) a radiation source incorporated into at least a portion of the surgical fastening device to render it radioactive; and c) a graft suitable for application to living tissue at the wound repair site. The graft is securable to the tissue with the surgical fastening device.

DETAILED DESCRIPTION OF EMBODIMENTS OF THE INVENTION

Figure 1:
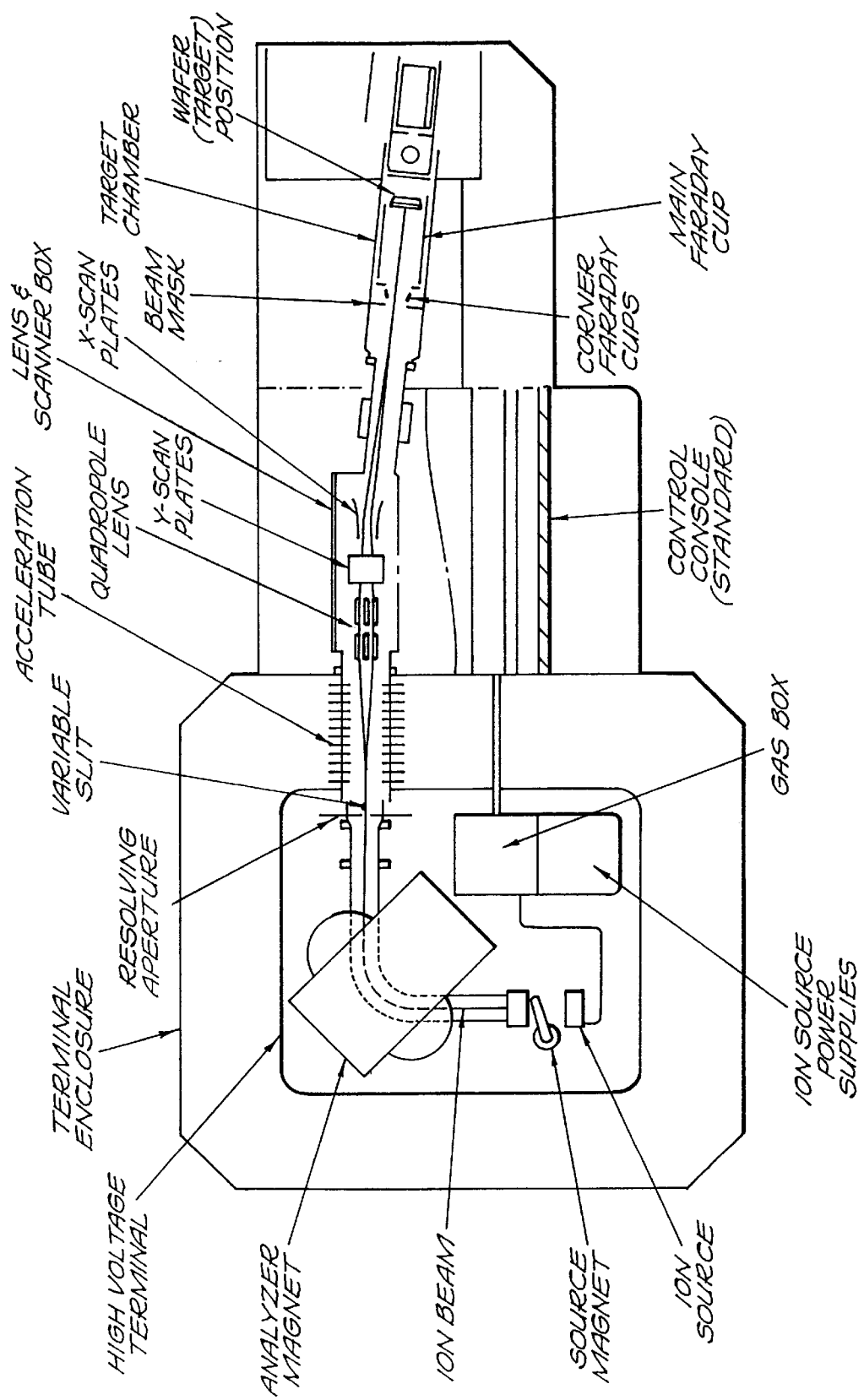
FIG. 1 is a schematic diagram of a mass analyzed ion implanter.

For maximum utility—which encompasses medical efficacy, economy and convenience—a radioisotope is desirably incorporated directly into a medical device, such as a surgical fastening device. This introduces some new considerations not previously encountered with the use of radioisotopes in health care.

First, it is essential that any radioisotope used for these purposes be where it is expected to be at all times and not be "shed" from the device incorporating it during its distribution and use.

Second, within that constraint, it must be possible to economically incorporate the radioisotope into a variety of materials conventionally used for the medical procedure in question. Such materials range from specialized plastics to metals and ceramics.

Third, the method must be capable of a high level of control, so as to ensure the quality, reproducibility and safety of the devices.

The method of ion implantation appears to meet these specific requirements, as well as those general requirements always encountered in the use of radioactivity.

The ion implantation approach can be utilized with almost any material capable of withstanding a vacuum. It can be utilized safely and economically, and it results in the radioisotope (or its precursor) being atomically dispersed into the surface of the substrate material, regardless of whether the substrate material is a plastic, metal or ceramic. The radioisotope is not a "coating" on the substrate in the usual sense, as there is no interface between the substrate and the added radioisotope material such that the latter can spall, flake, delaminate, or otherwise be separated from the underlying substrate material. Rather, the atoms of the radioisotope are dispersed within the atomic structure of the substrate and become an integral part of the substrate.

To further ensure that the radioisotope is fully incorporated into the substrate material and will not leach or spall off, a second layer of an encapsulating material, such as a metal, can be added to the substrate by similar techniques well-known in the art, such as, for example, ion beam assisted deposition (IBAD) or chemical vapor deposition (CVD). The encapsulating material must be a highly coherent, biocompatible material so that no radioactive material can migrate through the encapsulating layer. Suitable materials for the encapsulating layer include, for example, titanium, gold, platinum, palladium, stainless steel, nickel-titanium alloys, silica, alumina, and other biologically benign materials which are capable of acting as barriers to the migration, or diffusion, of the radioisotope concerned. The encapsulating material should form a strong bond with the substrate so that it will remain on the substrate during use.

The invention has application in the use of ion implantation for the development of medical devices which incorporate radioisotopes. In particular, the provision of radioactive surgical fastening devices, such as sutures, staples, clips, pins, plates, nails, screws, and patches in mesh or sheet form, is considered to be within the scope of the invention.

The type and method of ion implantation utilized in the present invention differs from conventional ion implantation methods used in the semiconductor industry in that semiconductor ion implantation typically involves only flat plate substrates, in the form of silicon wafers. In addition, high efficiency is not of paramount importance in semiconductor ion implantation. Perhaps most significantly, semiconductor ion implantation does not involve the use of radioisotopes. Thus, the ion implantation methods used in the present invention are believed to be novel to the extent that they must be tailored to satisfy the requirements of a heretofore unexplored application.

In the ion implantation process of the present invention, a filament in thermionic emission (with associated confinement) is used in an ion source to create a plasma. The positive ions produced in the plasma are extracted and accelerated in the presence of an electric field. A magnetic mass separator is used to select one particular isotope of an elemental species and deliver it to the work station, in which multiple devices to be treated are mounted. Finally, by using an electromagnetic focusing lens and raster scanning plates, the ion beam is focused and scanned onto the target, or substrate, material.

FIG. I shows a schematic diagram for a mass analyzed ion implanter. Energetic ions are directed to the surface of the target and typically penetrate a distance of 10 to 100 nanometers below the surface.

There are two possible methods of incorporating a radioisotope into a device by ion implantation. One method is to utilize a stable (i.e., non-radioactive) isotope for the ion implantation step, followed by conversion of that entity into the radioactive entity by transporting the device incorporating the stable isotope to a nuclear reactor for "activation" by exposing the device to a neutron flux. The latter method, while having been demonstrated as feasible, suffers from the severe disadvantages of complicating the logistics of the process and, most importantly, of risking the induction of undesired (and often dangerous) radioactive species by transmutation of trace impurities in the device.

An alternative method is the direct ion implantation of the radioisotope. For most radioisotopes, this is the method of choice, although it offers certain additional challenges. The success of this method depends at least in part on the efficiency of the ion source, which is critical, not only to minimize the usage of expensive radioactive material but also, and even more importantly, to minimize the level of contamination of the ion implantation system. A higher level of contamination can reduce the system utilization (throughput) by mandating downtime to allow the radiation level to "cool off."

It should be noted that the ion implantation of a non-metallic substrate material (using a form of ionizing radiation), and in particular a polymer, is generally not recommended, as the degrading effect of radiation on polymers is well-known. However, and somewhat counterintuitively, the ion implantation process of the present invention, in order to achieve useful levels of radiation, does not compromise the mechanical, chemical or surface properties of most substrate materials. The possibility of degradation of common substrate materials, either by the ion implantation process itself, or by the presence of anticipated levels of radioactivity within the device, is minimized, if not eliminated, in the present invention.

For example, it is known that an ion flux of $10^{14}$–$10^{15}$ ions/cm$^2$/sec will degrade polytetrafluoroethylene (PTFE). However, the ion flux required to achieve useful levels of radiation from the $^{32}$p isotope is in the range of $10^{10}$–$10^{11}$ ions/cm$^2$/sec, so no damage to the substrate is expected from the ion implantation process. Other types of polymers, such as polypropylene, commonly used as a suture material, are even more stable and thus even less susceptible to radiation damage at the levels of radiation necessary to achieve ion implantation thereof.

The ion implantation method of the present invention can be used to implant almost any element. The use of beta emitters for these applications, rather than the more penetrating gamma emitters, or mixtures of each, is envisioned. Typical beta emitting candidates for ion implantation include, for example, $^{45}$Ca, with a half-life of 165 days, $^{123}$Sn, with a half-life of 125 days, $^{89}$Sr, with a half-life of 51 days, $^{32}$p, with a half-life of 14.3 days, $^{90}$Sr/Y, with a half-life of 28 years, and $^{90}$Y, with a half-life of 2.7 days. Other candidates which may be suitable for particular applications include gamma emitters such as, for example, $^{125}$I, with a half-life of 60 days, $^{103}$Pd, with a half-life of 17 days, $^{192}$Ir, with a half-life of 75 days, and $^{57}$Co, with a half-life of 270 days. The particular requirements of a given application will determine the choice of isotope for implantation.

The ability to select from among a wide variety of radioisotopes is critical. For optimum therapeutic results, the variables of radiation type, radiation intensity, half-life and biological activity all need to be selected with the therapeutic objective (e.g., cancer treatment, avoidance of restenosis, avoidance of intimal hyperplasia), as well as the type of tissue, the extensiveness of the site to be treated, and the proximity of sensitive anatomy, in mind.

For example, for therapeutic indications involving only small localized sites, a beta emitter or a low-energy gamma ray emitter providing a relatively shallow penetration would be preferred. Candidates might include, for example, $^{45}$Ca, $^{123}$Sn, $^{89}$Sr, $^{32}$P, $^{33}$P, $^{103}$Pd, and $^{125}$I, although there other possibilities. For more extensive treatment areas, such as cancerous lesions, more deeply penetrating radiation is appropriate, such as from the gamma ray emitters $^{192}$Ir and $^{57}$Co. Additionally, the most appropriate radiation half-life may be dependent upon the type of treatment regimen required (i.e., chronic versus acute). Although the field of brachytherapy is relatively new, the need to select specific isotopes for specific medical and anatomical circumstances will likely become greater as more knowledge is obtained.

In general, beta (electron) emitters are preferred, since their characteristics are such that fully adequate protection of personnel can be assured, without significant interference with the conventional practices employed for non-radioactive device distribution and use. The beta (electron) emitting $^{32}$P radioisotope has an average energy of 0.69 MeV, which corresponds to a penetration of 2.5 mm in water, and less in tissue. The half-life of this isotope is 14.3 days, so the radiation level falls to a background level within a few months.

As an example, after 71 days, a 10 microcurie source would decay to 0.31 microcuries, which would be essentially equivalent to the radiation level of naturally-occurring $^{40}$K isotope, which, in a 70 kg person, would represent a radiation level of about 0.25 microcurie.

If relatively short half-life radioisotopes are employed, it is contemplated that the products of the invention will be delivered and used while the rapidly-decaying radioactivity remains within the therapeutic range. Each device will be air-shipped to the surgical site according to time-of-use requirements and clearly labeled with radiation level vs. time information to ensure that the product is implanted only while the radiation level remains in the therapeutic range, together with the labeling required by nuclear safety regulations.

As previously mentioned, one of the desirable features of ion implantation is that the process creates essentially no perturbation of the substrate mechanical properties. It is therefore possible to carry out the process repeatedly without degradation. This is extremely important, because it is obvious that many devices will, for a variety of reasons, not be used while still appropriately active. Such devices would preferably be returned to the principle manufacturing facility for reprocessing and ultimate reuse.

Devices which may typically be used with such radioactive sutures include, for example, natural and synthetic grafts, A-V fistulas, drains, shunts, and the like.

Other surgical fastening devices which can be treated according to the method of the invention include staples, clips, pins, nails, screws, plates, barbs, anchors, and various types of patches in the form of, for example, mesh sheets butterfly strips, or other tissue joining structures. Such devices can be made of substantially non-metallic materials, including polymeric materials, as well as from metals.

This technology has obvious application in sutures for vascular grafts, access grafts for dialysis, and a variety of other medical devices which are sutured into place.

Several advantages of a radioactive suture are apparent. A radioactive suture would be relatively economical, as a suture is inherently less expensive to use than in implantable device. Moreover, a radioactive suture would allow a greater degree of freedom and flexibility respecting the placement and desired dosage level of the radiation. Furthermore, as mentioned, radioactivity can be incorporated into either permanent or biodegradable suture materials without compromising any of the mechanical, surface, or chemical properties of the material. As a consequence, any suture material which has already been approved for medical and surgical uses may be used to incorporate radiation according to the present invention. This has obvious benefits in the expeditious introduction of such sutures to the market.

A radioactive suture would allow radiation to be directed to the area of greatest need, regardless of the implanted device used with the suture. For example, intimal hyperplasia is known to originate at the ends of vascular grafts, so the use of radioactive sutures at such locations is likely to be effective in preventing restenosis at those locations. Also, the density of the stitches of a radioactive suture along an incision, graft or stent allows radiation to be provided in variable intensity levels along the suture path. In addition, a radioactive suture can be relatively easily shielded from personnel so that exposure to radioactivity is prevented.

Radioactive sutures are particularly useful in applications in which it is desired to minimize the formation of scar tissue, such as in cosmetic surgery. Also, they can be used as "markers" in biopsy procedures to locate certain structures or entities, such as tumors, within the body.

In general, radioactive fasteners may be advantageous in any type of anastamosis of the body's conduits, including blood vessels (arterial and venous), ducts, arteriotomy closures, and various patches for such conduits and tissue openings.

I claim:

1. A surgical fastening device capable of controlling cellular response to injury at a wound repair site, comprising:
   a) a biocompatible surgical fastening device adapted for joining tissue at or near said wound repair site; and
   b) a radiation source incorporated into at least a portion of said fastening device to render said device radioactive.

2. A surgical fastening device according to claim 1, wherein said radioactive device is adapted to be selectively positioned at said wound repair site for delivery of a predetermined dose of radiation to said wound repair site.

3. A surgical fastening device according to claim 1, wherein said surgical fastening device is selected from the group consisting of sutures, staples, clips, pins, nails, screws, plates, barbs, anchors, and patches.

4. A surgical fastening device according to claim 3, wherein said device is made of a metallic material.

5. A surgical fastening device according to claim 3, wherein said device is made of a substantially nonmetallic material.

6. A surgical fastening device according to claim 5, wherein said device is made of a polymeric material.

7. A surgical fastening device according to claim 5, wherein said device is made of a substantially bioabsorbable material.

8. A surgical fastening device according to claim 1, wherein said surgical fastening device is adapted for substantially permanent implantation in said patient.

9. A surgical fastening device according to claim 1, wherein said surgical fastening device is adapted for temporary or removable implantation in said patient.

10. A surgical fastening device according to claim 1, wherein said radiation source comprises a radioisotope which is adapted to be incorporated into said surgical fastening device by ion implantation.

11. A surgical fastening device according to claim 10, wherein said radioisotope is selected from the group consisting of $^{45}$Ca, $^{123}$Sn, $^{89}$Sr, $^{32}$P, $^{90}$Sr/Y, $^{90}$Y, $^{125}$I, $^{103}$Pd, $^{192}$Ir, and $^{57}$Co.

12. A surgical fastening device according to claim 10, wherein an encapsulating layer of a coherent, biocompatible, and relatively dense material is deposited onto the surface of the surgical fastening device after ion implantation of said radioisotope into said fastening device.

13. A surgical fastening device according to claim 12, wherein said encapsulating layer comprises a biologically benign material selected from the group consisting of platinum, titanium, gold, palladium, stainless steel, nickel-titanium alloys, silica, and alumina.

14. A method of controlling cellular response to injury at a wound repair site, said method comprising the steps of:
   a. providing a surgical fastening device for controlling the cellular response to injury, said device including a biocompatible surgical fastening device adapted for joining tissue at or near said wound repair site, and a radiation source incorporated into at least a portion of said surgical fastening device to render said device radioactive; and
   b. implanting said surgical fastening device at or near said wound repair site,
   wherein said radiation source is selected to deliver a predetermined dose of radiation to said wound repair site over a predetermined period of time.

15. The method of claim 14, wherein said surgical fastening device is selected from the group consisting of sutures, staples, clips, pins, nails, screws, plates, barbs, anchors, and patches.

16. The method of claim 15, wherein said surgical fastening device is made of a metallic material.

17. The method of claim 15, wherein said surgical fastening device is made of a substantially non-metallic material.

18. The method of claim 14, wherein said surgical fastening device is a suture, and further comprising the steps of:
   c. providing a graft suitable for application to said wound repair site; and
   d. securing said graft to living tissue at said wound repair site with said suture, wherein a predetermined dose of radiation is delivered to the interface between said graft and said tissue over a predetermined period of time.

19. The method of claim 14, comprising the further step of:
   c. removing said surgical fastening device from said wound repair site after said predetermined dose of radiation has been delivered to said wound repair site.

20. The method of claim 19, comprising the further step of:
   d. reactivating said device by incorporating another radiation source into at least a portion of said device.

21. A kit for controlling cellular response to injury at a wound repair site, comprising:
   a) a biocompatible surgical fastening device adapted for joining tissue at or near said wound repair site;
   b) a radiation source incorporated into at least a portion of said surgical fastening device to render said device radioactive; and
   c) a graft suitable for application to living tissue at said wound repair site, wherein said graft is adapted to be secured to said tissue with said surgical fastening device.

22. A kit according to claim 21, wherein said surgical fastening device is selected from the group consisting of sutures, staples, clips, pins, nails, screws, plates, barbs, anchors, and patches.

23. A kit according to claim 22, wherein said surgical fastening device is made of a metallic material.

24. A kit according to claim 22, wherein said surgical fastening device is made of a substantially non-metallic material.

25. A kit according to claim 24, wherein said surgical fastening device is made of a polymeric material.

26. A kit according to claim 24, wherein said surgical fastening device is made of a substantially bioabsorbable material.

27. A kit according to claim 21, wherein said radiation source comprises a radioisotope which is adapted to be incorporated into said surgical fastening device by ion implantation.

28. A kit according to claim 27, wherein said radioisotope is selected from the group consisting of $^{45}$Ca, $^{123}$Sn, $^{89}$Sr, $^{32}$P, $^{90}$Sr/Y, $^{90}$Y, $^{125}$I, $^{103}$Pd, $^{192}$Ir, and $^{57}$Co.

29. A surgical fastening device capable of controlling cellular response to injury at a wound repair site, comprising:
   a) a biocompatible surgical fastening device adapted for joining tissue at or near said wound repair site; and
   b) a radiation source incorporated into at least a portion of said fastening device to render said device radioactive,
   wherein the device is made of a substantially bioabsorbable material.

30. A surgical fastening device according to claim 29, wherein said surgical fastening device is selected from the group consisting of sutures, staples, clips, pins, nails, screws, plates, barbs, anchors, and patches.

31. A surgical tissue joining device, comprising:
a) a biocompatible surgical tissue joining structure adapted for holding tissue together at or near said wound repair site; and
b) a radiation source incorporated into at least a portion of said tissue joining structure to render said device radioactive, so that the cellular response to injury at the wound repair site is controlled while tissue is held together by the tissue joining device.

32. A surgical tissue joining device according to claim 31, wherein said tissue joining device is selected from the group consisting of sutures, staples, clips, pins, nails, screws, plates, barbs, anchors, and patches.

* * * * *